United States Patent
Tanabe et al.

(10) Patent No.: US 11,925,753 B2
(45) Date of Patent: Mar. 12, 2024

(54) LIQUID ADMINISTERING DEVICE

(71) Applicant: FUNAI ELECTRIC CO., LTD., Osaka (JP)

(72) Inventors: Hideki Tanabe, Osaka (JP); Ryo Yonekawa, Osaka (JP); Naoki Motobayashi, Osaka (JP); Akihiro Azuma, Osaka (JP)

(73) Assignee: FUNAI ELECTRIC CO., LTD., Osaka (JP)

(*) Notice: Subject to any disclaimer, the term of this patent is extended or adjusted under 35 U.S.C. 154(b) by 214 days.

(21) Appl. No.: 17/246,712

(22) Filed: May 2, 2021

(65) Prior Publication Data

US 2021/0346622 A1    Nov. 11, 2021

(30) Foreign Application Priority Data

May 11, 2020 (JP) ................. 2020-083475

(51) Int. Cl.
*A61M 15/08* (2006.01)
(52) U.S. Cl.
CPC ......... *A61M 15/08* (2013.01); *A61M 2205/13* (2013.01); *A61M 2205/3327* (2013.01)
(58) Field of Classification Search
CPC .............. A61M 15/08; A61M 2205/13; A61M 2205/3327; A61M 2205/3306; A61M 2205/3375; A61M 2016/003; A61M 11/042
See application file for complete search history.

(56) References Cited

U.S. PATENT DOCUMENTS

| | | |
|---|---|---|
| 6,325,475 B1 | 12/2001 | Hayes et al. |
| 9,801,581 B2 | 10/2017 | Mills |
| 2003/0052196 A1* | 3/2003 | Fuchs ............... A61M 15/008 239/338 |
| 2019/0076100 A1 | 3/2019 | Narkiss et al. |

FOREIGN PATENT DOCUMENTS

| | | | |
|---|---|---|---|
| CM | 208756505 | 4/2019 | |
| GB | 2406283 | 3/2005 | |
| JP | 2016539679 | 12/2016 | |
| JP | 2018175136 | 11/2018 | |
| JP | 2019155064 | 9/2019 | |
| JP | 2020055560 | 4/2020 | |
| WO | 2014165694 | 10/2014 | |
| WO | WO-2014165694 A2 * | 10/2014 | ......... A61B 1/00045 |

* cited by examiner

*Primary Examiner* — Elliot S Ruddie
*Assistant Examiner* — Maap Ahmed Ellabib
(74) *Attorney, Agent, or Firm* — JCIPRNET (57) ABSTRACT

The disclosure provides a liquid administering device capable of accurately administering a liquid to a predetermined part in a nasal cavity. A liquid administering device 2 includes a main body 4, a first nozzle 6 that protrudes from the main body 4 in a predetermined direction and dispenses a liquid while being inserted into one nasal cavity 28a of a user, and a second nozzle 8 that protrudes from the main body 4 in the predetermined direction and is inserted into the other nasal cavity 28b of the user to position the first nozzle 6 with respect to one nasal cavity 28a.

2 Claims, 7 Drawing Sheets

LIQUID ADMINISTERING DEVICE

CROSS-REFERENCE TO RELATED APPLICATION

This application claims the priority benefits of Japanese application no. 2020-083475, filed on May 11, 2020. The entirety of the above-mentioned patent application is hereby incorporated by reference herein and made a part of this specification.

BACKGROUND

Technical Field

The disclosure relates to a liquid administering device for administering a liquid to a user.

Description of Related Art

A nasal spray is known for administering a liquid medicine to a nasal cavity of a user (for example, see Patent Document 1). The nasal spray includes a pump container filled with the liquid medicine and a spray head disposed at an upper end of the pump container.

The user manually presses down a lever of the spray head while inserting a tip of the spray head into one nasal cavity. Thereby, the liquid medicine in the pump container is dispensed from a hole at the tip of the spray head toward one nasal cavity.

RELATED ART

Patent Document

[Patent Document 1] Japanese Laid-Open No. 2020-055560

SUMMARY

Problems to be Solved

For the conventional nasal spray described above, the position of the tip of the spray head with respect to one nasal cavity may vary depending on how the user holds the nasal spray. Therefore, there arises a problem that it is difficult to accurately administer the liquid medicine to a predetermined part in the nasal cavity.

In view of the above, the disclosure provides a liquid administering device capable of accurately administering a liquid to a predetermined part in a nasal cavity.

Means for Solving the Problems

A liquid administering device according to an embodiment of the disclosure is adapted for administering a liquid to a user. The liquid administering device includes a main body, a first nozzle that protrudes from the main body in a predetermined direction and dispenses the liquid while being inserted into one nasal cavity of the user, and a second nozzle that protrudes from the main body in the predetermined direction and is inserted into the other nasal cavity of the user to position the first nozzle with respect to the one nasal cavity.

According to this embodiment, since the liquid administering device includes the second nozzle in addition to the first nozzle, by inserting the first nozzle into one nasal cavity and inserting the second nozzle into the other nasal cavity, the first nozzle can be positioned with respect to one nasal cavity. As a result, the liquid dispensed from the first nozzle can be accurately administered to a predetermined part in the nasal cavity.

For example, in the liquid administering device according to an embodiment of the disclosure, the liquid administering device may further include a sensor that detects an insertion state of at least one of the first nozzle and the second nozzle, and a dispensing controller that controls dispensation of the liquid from the first nozzle based on a detection result of the sensor.

According to this embodiment, the dispensation of the liquid from the first nozzle can be appropriately controlled based on the detection result of the sensor.

For example, in the liquid administering device according to an embodiment of the disclosure, the sensor may be disposed in the second nozzle and detect that the second nozzle is inserted into the other nasal cavity.

According to this embodiment, since the sensor is disposed in the second nozzle, the sensor can be prevented from interfering with the dispensation of the liquid from the first nozzle.

For example, in the liquid administering device according to an embodiment of the disclosure, the first nozzle may be formed in a tapered shape so that a tip of the first nozzle is tapered, and the second nozzle may be formed in a tapered shape so that a tip of the second nozzle is tapered.

According to this embodiment, the first nozzle and the second nozzle can be smoothly inserted into one nasal cavity and the other nasal cavity respectively.

Effects

With the liquid administering device according to an embodiment of the disclosure, the liquid can be accurately administered to the predetermined part in the nasal cavity.

DESCRIPTION OF THE EMBODIMENTS

Hereinafter, embodiments of the disclosure will be described in detail with reference to the drawings. It should be noted that all the embodiments described hereinafter show comprehensive or specific examples. The numerical values, shapes, materials, components, arrangement positions and connection forms of components, etc. shown in the following embodiments are examples and are not intended to limit the disclosure. In addition, among the components in the following embodiments, components not described in the independent claims are described as arbitrary components.

First Embodiment

1-1. Structure of Liquid Administering Device

Figure 1:
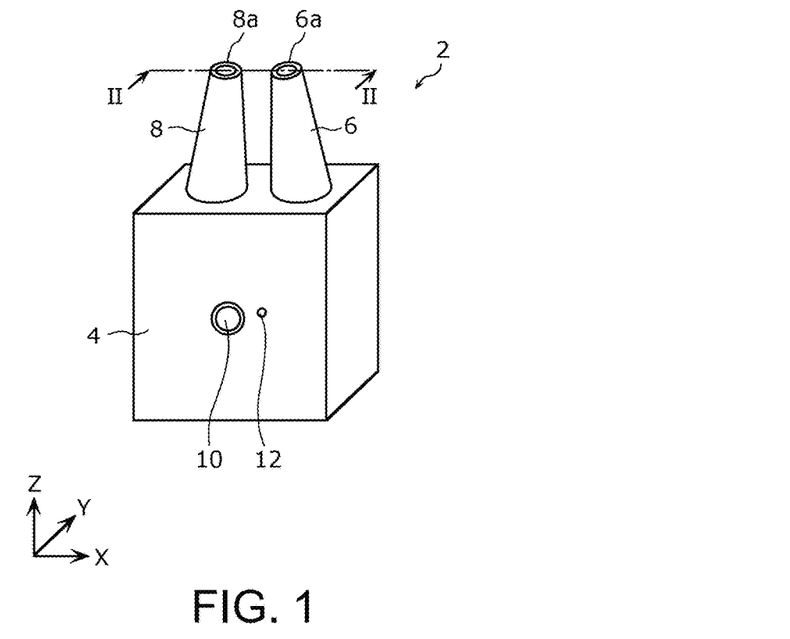
FIG. 1 is a perspective view showing a liquid administering device according to the first embodiment.
Figure 2:
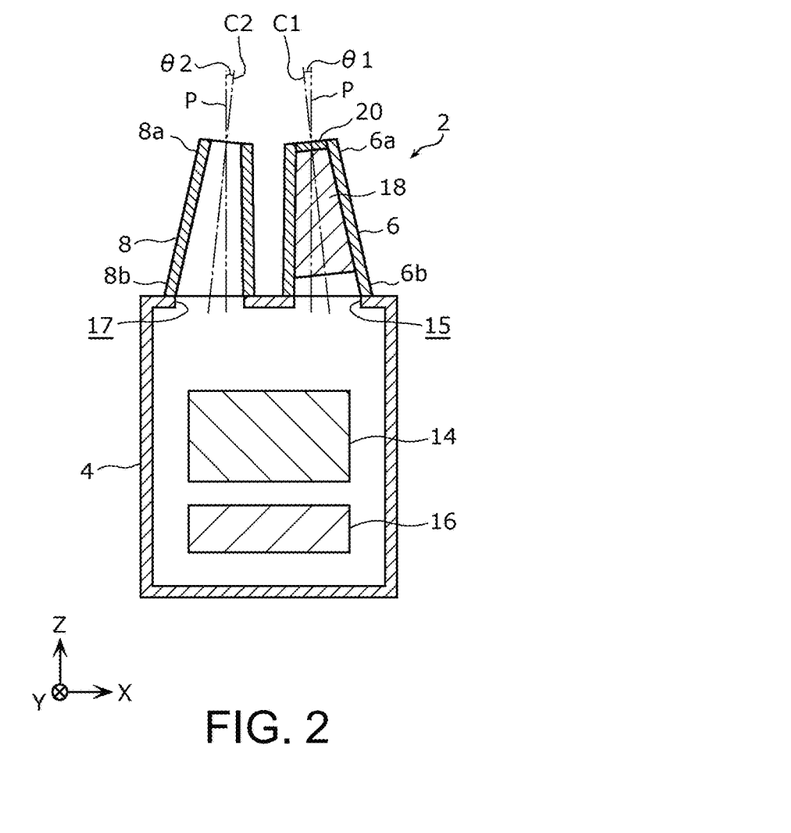
FIG. 2 is a schematic cross-sectional view of the liquid administering device according to the first embodiment along the line II-II of FIG. 1.

First, the structure of a liquid administering device 2 according to the first embodiment will be described with reference to FIG. 1 and FIG. 2. FIG. 1 is a perspective view showing the liquid administering device 2 according to the first embodiment. FIG. 2 is a schematic cross-sectional view of the liquid administering device 2 according to the first embodiment along the line II-II of FIG. 1.

In FIG. 1 and FIG. 2, a width direction (left-right direction) of the liquid administering device 2 is described as an X-axis direction, a depth direction (front-back direction) of the liquid administering device 2 is described as a Y-axis direction, and a height direction (up-down direction) of the liquid administering device 2 is described as a Z-axis direction.

The liquid administering device 2 is, for example, a nasal drop dispenser for administering a liquid medicine (an example of the liquid) to a nasal cavity 28 of a user (see FIG. 4 described later). As shown in FIG. 1, the liquid administering device 2 includes a main body 4, a first nozzle 6, and a second nozzle 8.

The main body 4 is formed in a hollow rectangular parallelepiped shape, for example. As shown in FIG. 1, an operation switch 10 and an indicator lamp 12 are disposed on a side surface of the main body 4. The operation switch 10 is a push switch for operating the liquid administering device 2. The user presses the operation switch 10, thereby dispensing the liquid medicine from a tip 6a of the first nozzle 6. The indicator lamp 12 is an LED (light emitting diode) lamp for displaying an operating state of the liquid administering device 2.

As shown in FIG. 2, a control board 14 and a battery 16 are disposed inside the main body 4. A control circuit, etc. for controlling the dispensation of the liquid medicine from the first nozzle 6 is mounted on the control board 14. The battery 16 supplies predetermined electric power to the indicator lamp 12, the control board 14, etc. Further, circular first opening 15 and second opening 17 communicating with the inside of the main body 4 are formed on an upper end surface of the main body 4.

The first nozzle 6 is a liquid medicine dispensing nozzle for dispensing the liquid medicine. The first nozzle 6 is formed in a cylindrical shape and is formed in a tapered shape so that the tip 6a is tapered. The first nozzle 6 protrudes from the upper end surface of the main body 4 in a predetermined direction (plus direction of the Z axis) and communicates with the first opening 15 of the main body 4. As shown in FIG. 2, a central axis C1 of the first nozzle 6 is tilted at an angle θ1 (0°<θ1≤10°) toward the side of the second nozzle 8 with respect to an axis P parallel to a central axis (Z-axis direction) of the main body 4.

As shown in FIG. 2, a cartridge 18 and a heater chip 20 are disposed inside the first nozzle 6. The cartridge 18 supplies the liquid medicine filled inside the cartridge 18 to the heater chip 20. The cartridge 18 is attachable to/detachable from the first nozzle 6. The heater chip 20 is disposed on the side of the tip 6a of the first nozzle 6 with respect to the cartridge 18. The heater chip 20 dispenses a predetermined amount (for example, about several tens of μliters) of atomized liquid medicine to the outside from the tip 6a of the first nozzle 6 by heating the liquid medicine supplied from the cartridge 18 by, for example, a thermal inkjet method.

The second nozzle 8 is a positioning auxiliary nozzle inserted into the other nasal cavity 28b of the user (see FIG. 4 described later) to position the first nozzle 6 with respect to one nasal cavity 28a (see FIG. 4 described later). The second nozzle 8 is formed in a cylindrical shape and is formed in a tapered shape so that a tip 8a is tapered. The second nozzle 8 protrudes from the upper end surface of the main body 4 in the predetermined direction and communicates with the second opening 17 of the main body 4. As shown in FIG. 2, a central axis C2 of the second nozzle 8 is tilted at an angle θ2 (0°<θ2≤10° toward the side of the first nozzle 6 with respect to the axis P parallel to the central axis of the main body 4. The angle θ2 is the same as the above-described angle θ1.

1-2. Functional Configuration of Liquid Administering Device

Figure 3:
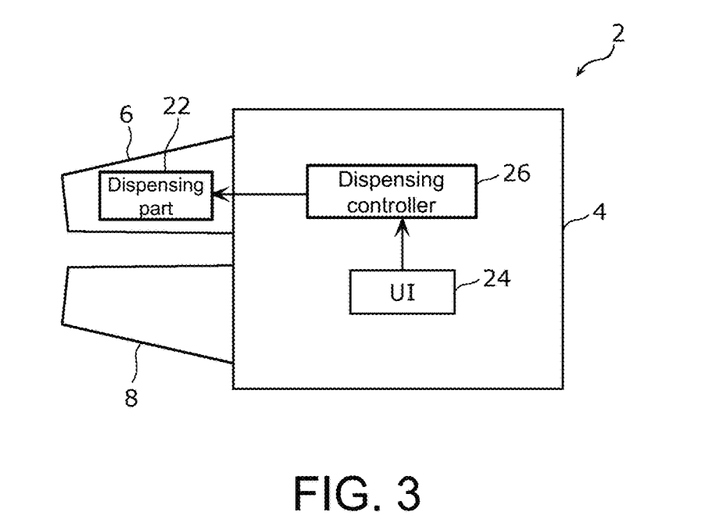
FIG. 3 is a block diagram showing the functional configuration of the liquid administering device according to the first embodiment.

Next, the functional configuration of the liquid administering device 2 according to the first embodiment will be described with reference to FIG. 3. FIG. 3 is a block diagram showing the functional configuration of the liquid administering device 2 according to the first embodiment.

As shown in FIG. 3, the liquid administering device 2 includes a dispensing part 22, a user interface (UI) 24, and a dispensing controller 26 as the functional configuration.

The dispensing part 22 includes the cartridge 18 and the heater chip 20 (see FIG. 2) described above and dispenses the liquid medicine from the tip 6a of the first nozzle 6 to the outside.

The user interface 24 includes the operation switch 10 (see FIG. 2) described above and receives an operation performed by the user on the liquid administering device 2.

The dispensing controller 26 includes the control board 14 (see FIG. 2) described above and controls the dispensation of the liquid medicine performed by the dispensing part 22 based on the operation received by the user interface 24. Specifically, when the user interface 24 receives the operation of a liquid medicine dispensation instruction performed by the user (that is, the operation switch 10 is pressed), the dispensing controller 26 controls the dispensing part 22 so that the liquid medicine is dispensed from the tip 6a of the first nozzle 6.

1-3. Method of Using Liquid Administering Device

Next, a method of using the liquid administering device 2 according to the first embodiment will be described with reference to FIG. 4 and FIG. 5. FIG. 4 and FIG. 5 are diagrams for illustrating the method of using the liquid administering device 2 according to the first embodiment.

Figure 4:
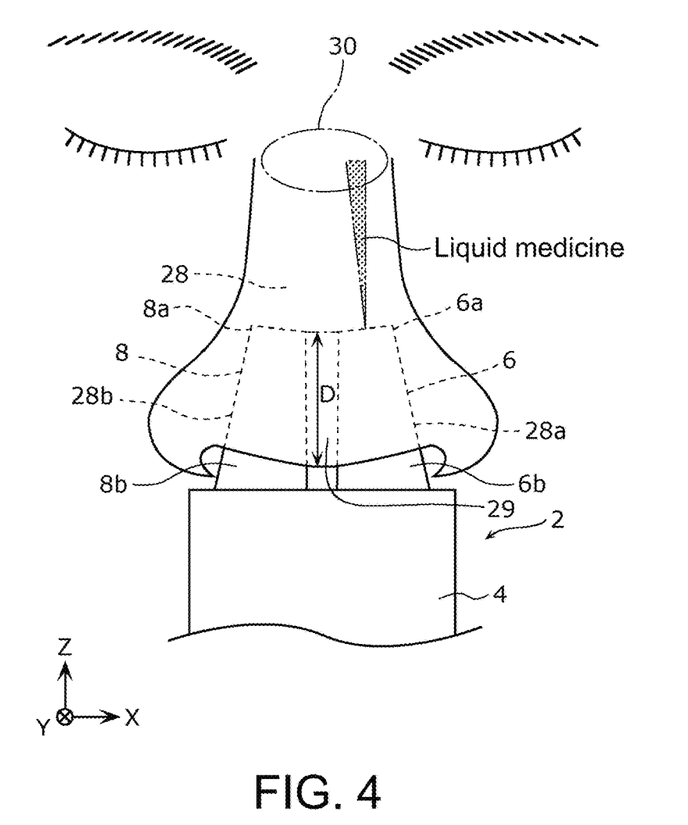
FIG. 4 is a diagram for illustrating a method of using the liquid administering device according to the first embodiment.
Figure 5:
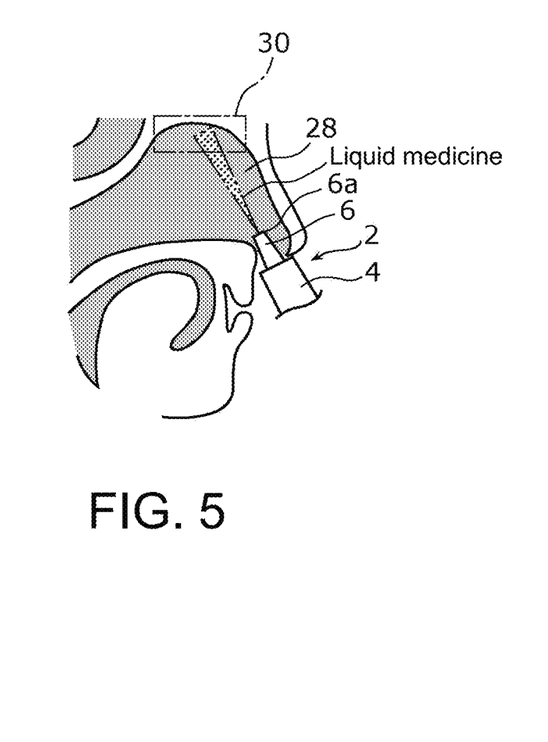
FIG. 5 is a diagram for illustrating a method of using the liquid administering device according to the first embodiment.

As shown in FIG. 4, the user inserts the first nozzle 6 into one (for example, left) nasal cavity 28a and inserts the second nozzle 8 into the other (for example, right) nasal cavity 28b while holding the main body 4 by hand. By inserting the second nozzle 8 into the other nasal cavity 28b in this way, the first nozzle 6 is positioned with respect to one nasal cavity 28a. Further, as shown in FIG. 5, an outer surface of the first nozzle 6 is guided along an inner wall of one nasal cavity 28a and an outer surface of the second nozzle 8 is guided along an inner wall of the other nasal cavity 28b. Thereby, the tip 6a of the first nozzle 6 faces a predetermined part 30 (for example, olfactory region) in the nasal cavity 28. The nasal cavity 28 means a nasal cavity on the back side of one nasal cavity 28a and the other nasal cavity 28b.

At this time, as shown in FIG. 4, a nasal septum 29 of the user comes into contact with a part between a base end 6b (an end opposite to the tip 6a) of the first nozzle 6 and a base end 8b (an end opposite to the tip 8a) of the second nozzle 8, by which an insertion depth D of each of the first nozzle 6 and the second nozzle 8 is restricted to, for example, 20 mm or less.

In this state, the user presses the operation switch 10 with a finger, thereby dispensing the liquid medicine from the tip 6a of the first nozzle 6. As shown in FIG. 5, the liquid medicine dispensed from the tip 6a of the first nozzle 6 adheres to the predetermined part 30 in the nasal cavity 28 and is administered.

1-4. Effect

As described above, the liquid administering device 2 of this embodiment includes the second nozzle 8 in addition to the first nozzle 6. By inserting the first nozzle 6 into one nasal cavity 28a and inserting the second nozzle 8 into the other nasal cavity 28b, the first nozzle 6 can be positioned with respect to one nasal cavity 28a. As a result, the liquid medicine dispensed from the tip 6a of the first nozzle 6 can be accurately administered to the predetermined part 30 in the nasal cavity 28.

For example, if the liquid medicine is a therapeutic drug for central nervous system diseases such as Alzheimer's disease, in order for the liquid medicine to function optimally, it is necessary to accurately administer the liquid medicine to the olfactory region, which is the predetermined part 30 in the nasal cavity 28. The liquid administering device 2 of this embodiment is particularly useful for applications in such cases. Nevertheless, the liquid medicine is not limited to the therapeutic drug for central nervous system diseases and may be, for example, a rhinitis drug.

Second Embodiment

Figure 6:
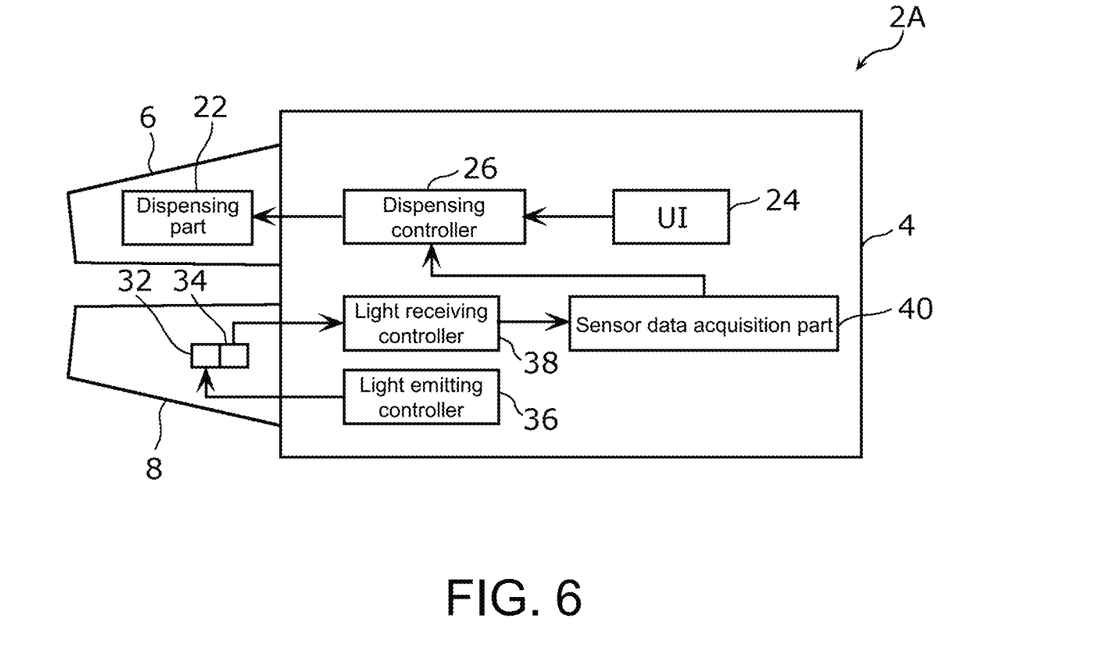
FIG. 6 is a block diagram showing the functional configuration of a liquid administering device according to the second embodiment.
Figure 7:
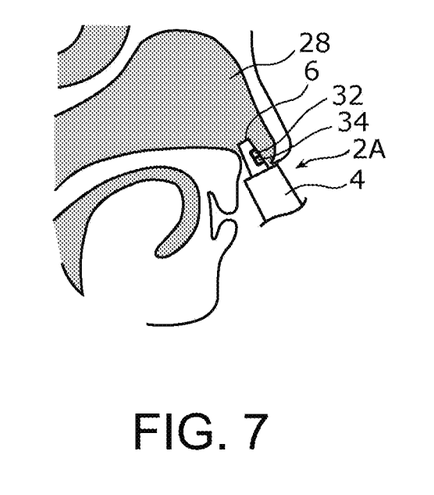
FIG. 7 is a diagram for illustrating a method of using the liquid administering device according to the second embodiment.

The functional configuration of a liquid administering device 2A according to the second embodiment will be described with reference to FIG. 6 and FIG. 7. FIG. 6 is a block diagram showing the functional configuration of the liquid administering device 2A according to the second embodiment. FIG. 7 is a diagram for illustrating a method of using the liquid administering device 2A according to the second embodiment. In the following embodiments, the same components as those of the first embodiment are denoted by the same reference numerals and the description thereof is omitted.

As shown in FIG. 6, the liquid administering device 2A according to the second embodiment differs from the first embodiment in that the liquid administering device 2A includes a light emitting part 32 (an example of the sensor), a light receiving part 34 (an example of the sensor), a light emitting controller 36, a light receiving controller 38, and a sensor data acquisition part 40.

The light emitting part 32 and the light receiving part 34 are reflection type optical sensors for detecting the insertion state of the second nozzle 8 into the other nasal cavity 28b (see FIG. 4 described above) and are disposed adjacent to each other on the outer surface of the second nozzle 8. The light emitting part 32 is an LED and the light receiving part 34 is a phototransistor.

The light emitting controller 36 controls the light emission of the light emitting part 32. When the light receiving part 34 receives the light from the light emitting part 32, the light receiving controller 38 outputs a detection signal indicating that the second nozzle 8 is inserted into the other nasal cavity 28b to the sensor data acquisition part 40.

When the sensor data acquisition part 40 receives the detection signal from the light receiving controller 38, the sensor data acquisition part 40 outputs a dispensation permission signal for permitting the dispensation of the liquid medicine to the dispensing controller 26.

In a state where the user does not insert the first nozzle 6 and the second nozzle 8 into one nasal cavity 28a and the other nasal cavity 28b respectively, the light receiving part 34 does not receive the light from the light emitting part 32 so the light receiving controller 38 does not output the detection signal to the sensor data acquisition part 40. The sensor data acquisition part 40 does not output the dispensation permission signal to the dispensing controller 26 when not receiving the detection signal from the light receiving controller 38. In this state, even if the user presses the operation switch 10, the dispensing controller 26 controls the dispensing part 22 not to dispense the liquid medicine.

On the other hand, as shown in FIG. 7, when the user inserts the first nozzle 6 and the second nozzle 8 into one nasal cavity 28a and the other nasal cavity 28b respectively, the light from the light emitting part 32 is reflected by the inner wall of the other nasal cavity 28b and then received by the light receiving part 34. Thereby, the light receiving controller 38 outputs the detection signal to the sensor data acquisition part 40. The sensor data acquisition part 40 outputs the dispensation permission signal to the dispensing controller 26 with the reception of the detection signal from the light receiving controller 38 as a trigger. When the user presses the operation switch 10 in this state, the dispensing controller 26 controls the dispensing part 22 to dispense the liquid medicine.

Accordingly, in this embodiment, when the operation switch 10 is erroneously pressed before the user inserts the first nozzle 6 and the second nozzle 8 into one nasal cavity 28a and the other nasal cavity 28b respectively, the liquid medicine can be prevented from being dispensed from the first nozzle 6.

Third Embodiment

Figure 8:
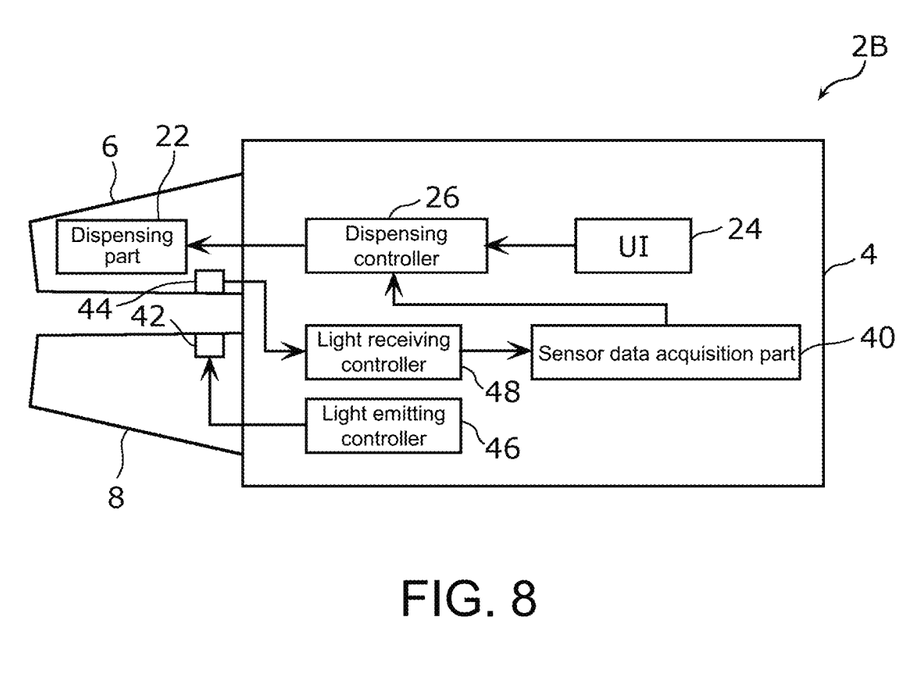
FIG. 8 is a block diagram showing the functional configuration of a liquid administering device according to the third embodiment.
Figure 9:
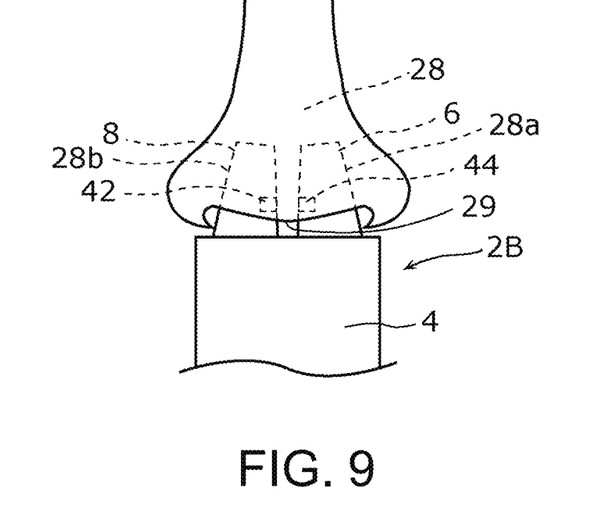
FIG. 9 is a diagram for illustrating a method of using the liquid administering device according to the third embodiment.

The functional configuration of a liquid administering device 2B according to the third embodiment will be described with reference to FIG. 8 and FIG. 9. FIG. 8 is a block diagram showing the functional configuration of the liquid administering device 2B according to the third embodiment. FIG. 9 is a diagram for illustrating a method of using the liquid administering device 2B according to the third embodiment.

As shown in FIG. 8, the liquid administering device 2B according to the third embodiment differs from the first embodiment in that the liquid administering device 2B includes a light emitting part 42 (an example of the sensor), a light receiving part 44 (an example of the sensor), a light emitting controller 46, a light receiving controller 48, and a sensor data acquisition part 40.

The light emitting part 42 and the light receiving part 44 are light blocking type optical sensors for respectively detecting the insertion state of the first nozzle 6 into one nasal cavity 28a (see FIG. 4 described above) and the insertion state of the second nozzle 8 into the other nasal cavity 28b (see FIG. 4 described above). The light emitting part 42 is disposed on the outer surface of the second nozzle 8. The light receiving part 44 is disposed on the outer surface of the first nozzle 6 and is disposed to face the light emitting part 42. The light emitting part 42 is an LED and the light receiving part 44 is a phototransistor.

The light emitting controller 46 controls the light emission of the light emitting part 42. When the light receiving part 44 stops receiving the light from the light emitting part 42, the light receiving controller 48 outputs a detection signal indicating that the first nozzle 6 and the second nozzle 8 are inserted into one nasal cavity 28a and the other nasal cavity 28b respectively to the sensor data acquisition part 40.

When the sensor data acquisition part 40 receives the detection signal from the light receiving controller 48, the sensor data acquisition part 40 outputs a dispensation permission signal for permitting the dispensation of the liquid medicine to the dispensing controller 26.

In a state where the user does not insert the first nozzle 6 and the second nozzle 8 into one nasal cavity 28a and the other nasal cavity 28b respectively, the light receiving part 44 directly receives the light from the light emitting part 42 so the light receiving controller 48 does not output the detection signal to the sensor data acquisition part 40. The sensor data acquisition part 40 does not output the dispensation permission signal to the dispensing controller 26 when not receiving the detection signal from the light receiving controller 48. In this state, even if the user presses the operation switch 10, the dispensing controller 26 controls the dispensing part 22 not to dispense the liquid medicine.

On the other hand, as shown in FIG. 9, when the user inserts the first nozzle 6 and the second nozzle 8 into one nasal cavity 28a and the other nasal cavity 28b respectively, the light from the light emitting part 42 is blocked by the nasal septum 29 so the light receiving part 44 does not receive the light from the light emitting part 42. Thereby, the light receiving controller 48 outputs the detection signal to the sensor data acquisition part 40. The sensor data acquisition part 40 outputs the dispensation permission signal to the dispensing controller 26 with the reception of the detection signal from the light receiving controller 48 as a trigger. When the user presses the operation switch 10 in this state, the dispensing controller 26 controls the dispensing part 22 to dispense the liquid medicine.

Accordingly, the same effect as that of the second embodiment can also be obtained in this embodiment.

Fourth Embodiment

Figure 10:
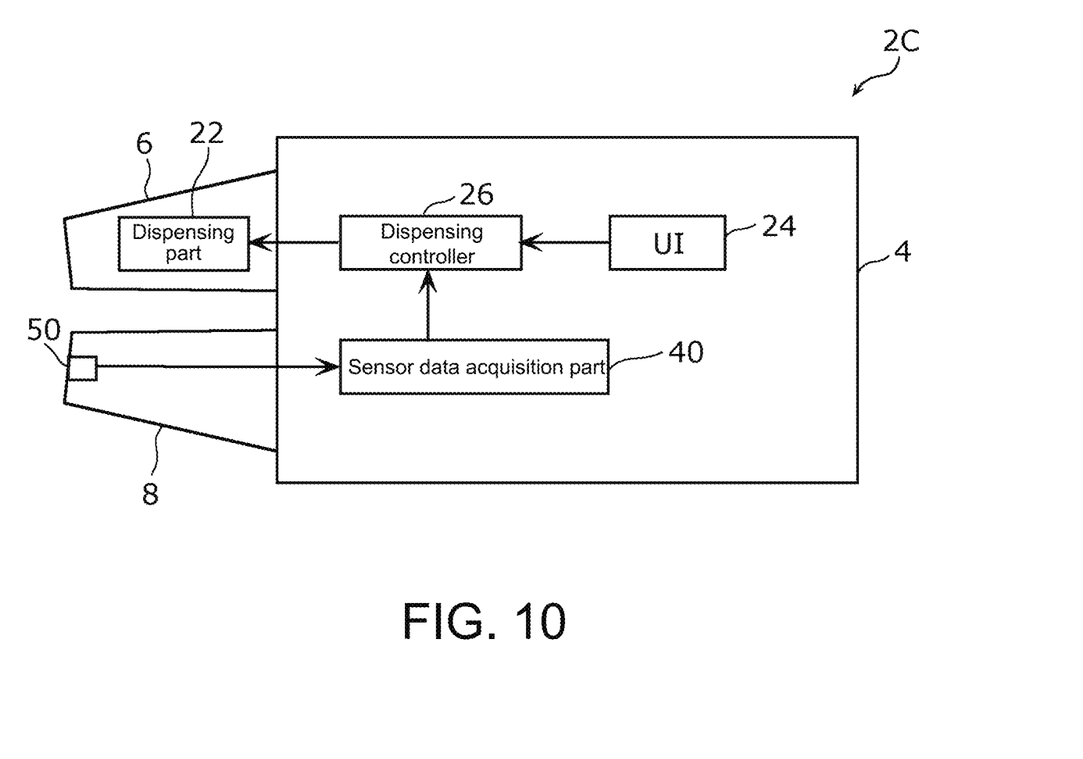
FIG. 10 is a block diagram showing the functional configuration of a liquid administering device according to the fourth embodiment.
Figure 11:
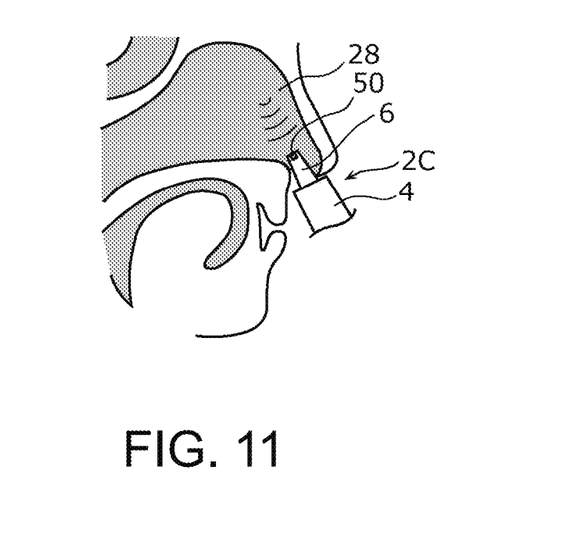
FIG. 11 is a diagram for illustrating a method of using the liquid administering device according to the fourth embodiment.

The functional configuration of a liquid administering device 2C according to the fourth embodiment will be described with reference to FIG. 10 and FIG. 11. FIG. 10 is a block diagram showing the functional configuration of the liquid administering device 2C according to the fourth embodiment. FIG. 11 is a diagram for illustrating a method of using the liquid administering device 2C according to the fourth embodiment.

As shown in FIG. 10, the liquid administering device 2C according to the fourth embodiment differs from the first embodiment in that the liquid administering device 2C includes an infrared sensor 50 (an example of the sensor) and a sensor data acquisition part 40.

The infrared sensor 50 is a thermopile for detecting the insertion state of the second nozzle 8 into the other nasal cavity 28b (see FIG. 4 described above). The infrared sensor 50 is disposed at the tip of the second nozzle 8 and outputs a detection signal indicating that the second nozzle 8 is inserted into the other nasal cavity 28b to the sensor data acquisition part 40 when receiving infrared rays from the nasal cavity 28.

When the sensor data acquisition part 40 receives the detection signal from the infrared sensor 50, the sensor data acquisition part 40 outputs a dispensation permission signal for permitting the dispensation of the liquid medicine to the dispensing controller 26.

In a state where the user does not insert the first nozzle 6 and the second nozzle 8 into one nasal cavity 28a and the other nasal cavity 28b respectively, the infrared sensor 50 does not receive the infrared rays from the nasal cavity 28 so the infrared sensor 50 does not output the detection signal to the sensor data acquisition part 40. The sensor data acquisition part 40 does not output the dispensation permission signal to the dispensing controller 26 when not receiving the detection signal from the infrared sensor 50. In this state, even if the user presses the operation switch 10, the dispensing controller 26 controls the dispensing part 22 not to dispense the liquid medicine.

On the other hand, as shown in FIG. 11, when the user inserts the first nozzle 6 and the second nozzle 8 into one nasal cavity 28a and the other nasal cavity 28b respectively, the infrared sensor 50 receives the infrared rays from the nasal cavity 28 and outputs the detection signal to the sensor data acquisition part 40. The sensor data acquisition part 40 outputs the dispensation permission signal to the dispensing controller 26 with the reception of the detection signal from the infrared sensor 50 as a trigger. When the user presses the operation switch 10 in this state, the dispensing controller 26 controls the dispensing part 22 to dispense the liquid medicine.

Accordingly, the same effect as that of the second embodiment can also be obtained in this embodiment.

Fifth Embodiment

Figure 12:
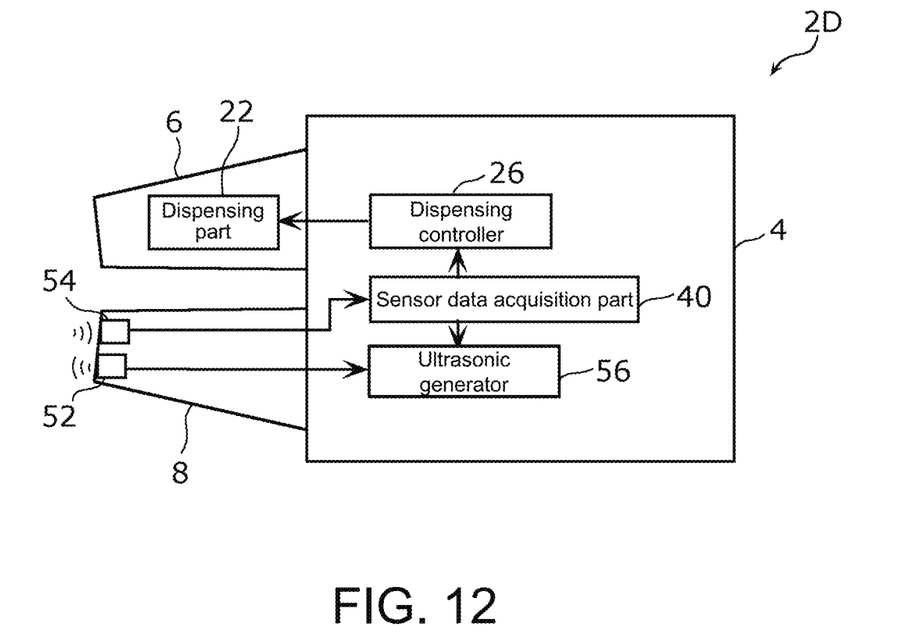
FIG. 12 is a block diagram showing the functional configuration of a liquid administering device according to the fifth embodiment.
Figure 13:
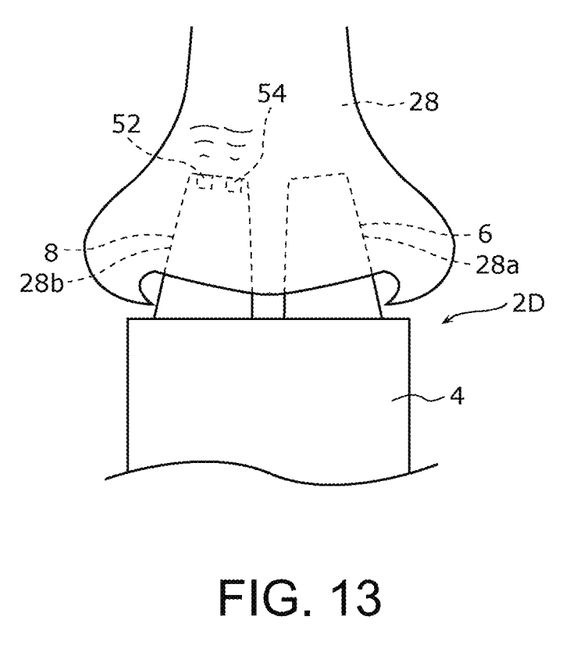
FIG. 13 is a diagram for illustrating a method of using the liquid administering device according to the fifth embodiment.

The functional configuration of a liquid administering device 2D according to the fifth embodiment will be described with reference to FIG. 12 and FIG. 13. FIG. 12 is a block diagram showing the functional configuration of the liquid administering device 2D according to the fifth embodiment. FIG. 13 is a diagram for illustrating a method of using the liquid administering device 2D according to the fifth embodiment.

As shown in FIG. 12, the liquid administering device 2D according to the fifth embodiment differs from the first embodiment in that the liquid administering device 2D includes a sound generator 52, an ultrasonic sensor 54 (an example of the sensor), an ultrasonic generator 56, and a sensor data acquisition part 40. Further, the liquid administering device 2D according to the fifth embodiment differs from the first embodiment in that the liquid administering device 2D does not include the user interface 24.

The ultrasonic generator 56 generates ultrasonic waves and outputs the generated ultrasonic waves to the sound generator 52. The sound generator 52 is a piezoelectric sound generator that outputs the ultrasonic waves from the ultrasonic generator 56 to the outside and is disposed at the tip of the second nozzle 8. The ultrasonic sensor 54 is a piezoelectric ultrasonic sensor for detecting the insertion state of the second nozzle 8 into the other nasal cavity 28b (see FIG. 4 described above). When the ultrasonic sensor 54 receives the ultrasonic waves from the sound generator 52, the ultrasonic sensor 54 outputs a detection signal indicating that the second nozzle 8 is inserted into the other nasal cavity 28b to the sensor data acquisition part 40.

In this embodiment, the sound generator 52 and the ultrasonic sensor 54 are separately configured, but the disclosure is not limited thereto. For example, by driving one piezoelectric element in a time-division manner, the function of the sound generator 52 and the function of the ultrasonic sensor 54 may be combined.

When the sensor data acquisition part 40 receives the detection signal from the ultrasonic sensor 54, the sensor data acquisition part 40 outputs a dispensation instruction signal for instructing the dispensation of the liquid medicine to the dispensing controller 26.

In a state where the user does not insert the first nozzle 6 and the second nozzle 8 into one nasal cavity 28a and the other nasal cavity 28b respectively, the ultrasonic sensor 54 does not receive the ultrasonic waves from the sound generator 52 so the ultrasonic sensor 54 does not output the detection signal to the sensor data acquisition part 40. The sensor data acquisition part 40 does not output the dispensation instruction signal to the dispensing controller 26 when not receiving the detection signal from the ultrasonic sensor 54. Thereby, the dispensing controller 26 controls the dispensing part 22 not to dispense the liquid medicine.

On the other hand, as shown in FIG. 13, when the user inserts the first nozzle 6 and the second nozzle 8 into one nasal cavity 28a and the other nasal cavity 28b respectively, the ultrasonic waves from the sound generator 52 is reflected by the nasal cavity 28 and then received by the ultrasonic sensor 54. Thereby, the ultrasonic sensor 54 outputs the detection signal to the sensor data acquisition part 40. The sensor data acquisition part 40 outputs the dispensation instruction signal to the dispensing controller 26 with the reception of the detection signal from the ultrasonic sensor 54 as a trigger. Thereby, the dispensing controller 26 controls the dispensing part 22 to dispense the liquid medicine.

Accordingly, with the liquid administering device 2D of this embodiment, the user can automatically dispense the liquid medicine from the first nozzle 6 simply by inserting the first nozzle 6 and the second nozzle 8 into one nasal cavity 28a and the other nasal cavity 28b respectively. As a result, it can save the trouble of operating the operation switch 10 (see FIG. 1) described above and improve the convenience.

Modified Example

Although the liquid administering devices according to the first to fifth embodiments of the disclosure have been described above, the disclosure is not limited to the above embodiments. For example, the above embodiments may be combined respectively.

In each of the above embodiments, the liquid administered to the user by the liquid administering device 2 (2A, 2B, 2C, 2D) is a liquid medicine, but the disclosure is not limited thereto. For example, the liquid may be a liquid having a relaxing fragrance or a stimulating liquid having a wakefulness effect.

In each of the above embodiments, the second nozzle 8 is formed in a cylindrical shape, but the disclosure is not limited thereto. For example, the second nozzle 8 may be formed in a solid rod shape.

In the above second, fourth, and fifth embodiments, various sensors are disposed only in the second nozzle 8, but the disclosure is not limited thereto, and various sensors may be disposed in both the first nozzle 6 and the second nozzle 8. Thereby, the insertion state of the first nozzle 6 into one nasal cavity 28a and the insertion state of the second nozzle 8 into the other nasal cavity 28b can be detected more reliably.

Further, a flow rate sensor for detecting the inhalation of the user may be disposed in the second nozzle 8. The dispensing controller 26 may control the dispensing part 22 to dispense the liquid medicine at a timing when the flow rate sensor does not detect the inhalation of the user (that is, the user stops breathing). Thereby, when the user inhales the liquid medicine deeply, the liquid medicine can be suppressed from flowing into the lungs of the user, and the liquid medicine can be reliably administered to the predetermined part 30 in the nasal cavity 28.

INDUSTRIAL APPLICABILITY

The liquid administering device according to the disclosure can be used as a nasal drop dispenser for administering a liquid medicine to a nasal cavity of a user, for example.

What is claimed is:
1. A liquid administering device for administering a liquid to a user, the liquid administering device comprising:
 a main body;
 a first nozzle protruding from the main body in a predetermined direction and configured to be inserted into one nasal cavity of the user to dispense the liquid;
 a second nozzle protruding from the main body in the predetermined direction and configured to be inserted into the other nasal cavity of the user to position the first nozzle with respect to the one nasal cavity;
 a sensor detecting an insertion state of at least one of the first nozzle and the second nozzle, wherein the sensor is disposed in the second nozzle and configured to detect the second nozzle is inserted into the other nasal cavity;
 a dispensing controller controlling dispensation of the liquid from the first nozzle based on a detection result of the sensor; and
 a dispensing part comprising a cartridge and a heater chip disposed inside the first nozzle, wherein the cartridge supplies the liquid filled inside the cartridge to the heater chip so that the liquid is heated and dispensed from heater chip based on a control of the dispensing controller.

2. The liquid administering device according to claim 1, wherein the first nozzle is formed in a tapered shape so that a tip of the first nozzle is tapered, and
the second nozzle is formed in a tapered shape so that a tip of the second nozzle is tapered.

* * * * *